(12) United States Patent
Hoock et al.

(10) Patent No.: US 8,183,267 B2
(45) Date of Patent: May 22, 2012

(54) CARBOXYLIC ACID SALTS OF 2-AMINO-3-CARBETHOXYAMINO-6-(4-FLUORO-BENZYLAMINO)-PYRIDINE

(75) Inventors: Christoph Martin Hoock, Dresden (DE); Asal Qadan, Dresden (DE)

(73) Assignee: AWD. Pharma GmbH & Co. KG, Radebeul (DE)

(*) Notice: Subject to any disclaimer, the term of this patent is extended or adjusted under 35 U.S.C. 154(b) by 241 days.

(21) Appl. No.: 12/481,414

(22) Filed: Jun. 9, 2009

(65) Prior Publication Data
US 2009/0306150 A1    Dec. 10, 2009

(30) Foreign Application Priority Data
Jun. 9, 2008  (EP) .................................... 08010472

(51) Int. Cl.
C07D 213/02    (2006.01)
A61K 31/44     (2006.01)

(52) U.S. Cl. ........................ 514/352; 546/308
(58) Field of Classification Search .................. None
See application file for complete search history.

(56) References Cited

U.S. PATENT DOCUMENTS

| | | | | |
|---|---|---|---|---|
| 5,959,115 | A * | 9/1999 | Olbrich et al. | 546/308 |
| 6,770,678 | B1 * | 8/2004 | Kurz et al. | 514/634 |
| 2006/0252804 | A1 * | 11/2006 | Pieroth et al. | 514/352 |

FOREIGN PATENT DOCUMENTS

| | | |
|---|---|---|
| DE | 17 95 858 | 4/1978 |
| DE | 31 33 519 | 6/1982 |
| DE | 33 37 593 | 5/1984 |
| DE | 39 15 184 | 11/1989 |
| EP | 0 160 865 | 11/1985 |
| EP | 0 615 754 | 7/2002 |
| EP | 0 977 736 | 9/2003 |
| EP | 1 795 186 | 6/2007 |
| EP | 08010472.2 | * 6/2008 |
| WO | WO 2004/112754 | 12/2004 |

OTHER PUBLICATIONS

Hoock et al, PCT/US2009/046775 filed Jun. 9, 2009.*
Kuhnert-Brandst, M. et al "Contribution to Polymorphism of Drugs 7th Communication: Famotidine, Flupirtine Maleate, GYKI-51189, Paxamate, Propentofylline, and Triclabendazole" Scientia Pharmaceutica, vol. 58, p. 55-67, (1990).
Caira, M.R. "Crystalline Polymorphism of Organic Compounds", Topics in Current Chemistry, vol. 198, p. 163-208, (1998).
Landgraf, K.F. et al. "Polymorphism and desolvation of flupirtine maleate", European Journal of Pharmaceutics and Biopharmaceutics, vol. 46, p. 329-337, (1998).

* cited by examiner

*Primary Examiner* — Zinna Northington Davis
(74) *Attorney, Agent, or Firm* — Arent Fox LLP (57) ABSTRACT

The preparation of flupirtine carboxylate acid addition salts having the following formula (2),

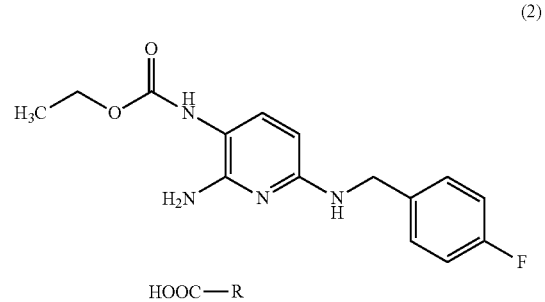

wherein R represents hydrogen or a $C_1$-$C_6$ alkyl group, with the proviso that RCOOH is neither maleic acid nor gluconic acid, is described.

5 Claims, 8 Drawing Sheets

CARBOXYLIC ACID SALTS OF 2-AMINO-3-CARBETHOXYAMINO-6-(4-FLUORO-BENZYLAMINO)-PYRIDINE

CROSS-REFERENCE TO RELATED APPLICATIONS

This application claims the benefit of European patent application no. 08010472.2, filed Jun. 9, 2008, which is incorporated herein by reference in its entirety.

TECHNICAL FIELD

The present invention relates to carboxylate addition salts of flupirtine, process for preparing them and pharmaceutical compositions comprising thereof, and to therapeutic uses thereof.

BACKGROUND 2-amino-3-carbethoxyamino-6-(4-fluoro-benzylamino)-pyridine ("Flupirtine") of the following formula (1):

(1)

is a centrally active non-opioid analgesic which does not cause any addiction or tolerance development. It is also a muscle-relaxant.

Flupirtine has a unique spectrum of pharmacological activity. It is used in the treatment and prevention of acute and chronic pain including neuropathic pain, nerve pain, cancer pain, vasomotor and migraine headaches, post-operative pain, post-traumatic pain, burn pain, erosion pain, dental pain and the pain associated with degenerative and inflammatory joint disease.

Flupirtine is also used in the treatment and prevention of muscular tension, muscle spasm and muscle stiffness. It is particularly useful in the treatment of back pain. Additionally, flupirtine also exerts potent cyto- and neuroprotective effects and has utility in the treatment and prevention of neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant types and Batten disease. Flupirtine also has utility in the treatment and prevention of diseases of the eye such as maculopathy including senile macular degeneration, diabetic retinopathy, glaucoma and retinitis pigmentosa. Flupirtine also has utility in the treatment and prevention of myocardial ischemia and infarction, cerebral ischemia and infarction, shock, tinnitus and hepatitis.

Flupirtine is commonly used in the form of pharmaceutically acceptable acid addition salts. Commercially, flupirtine is available as its maleate addition salt under the trademark Katadolon®. There are two known polymorphs of flupirtine maleate, designated in the art as flupirtine maleate A and B.

European patent EP 0 977 736 discloses pure flupirtine maleate crystalline form A and a process for its preparation. Flupirtine and mixtures of flupirtine maleate polymorphs A and B and pure polymorph B can be synthesised according to DE 3133519.

Other known flupirtine salts are flupirtine chloride, reported in German patent DE 1 795 858, and flupirtine gluconate, reported in European patent EP 0 160 865. WO 2004/112754 discloses several acid addition salts of flupirtine and their use in lyophilisates for parenteral solutions. For example, the flupirtin gluconate acid addition salt was prepared by lyophilisation and obtained in amorphous form.

Polymorphs A and B of flupirtine maleate are both characterized by an acicular morphology. The extremely fine needle structure of flupirtine maleate poses difficulties in the formulation process as is, for example, reported in EP 1 795 186. In particular, the acicular structure poses difficulties in the development of controlled release formulations of flupirtine as is described in patents EP 0 615 754 and EP 1 795 186. Furthermore, due to the acicular morphology, polymorphs A and B of flupirtine maleate have a very low bulk density and poor flowability causing difficulties in the formulation process. As a consequence, dosing of flupirtine maleate is difficult and the reproducibility of the formulation process is poor. These characteristics of flupirtine maleate necessitate a costly additional mechanical treatment of the drug substance for proper further processing.

The present invention addresses the need of providing other flupirtine acid addition salts, such as carboxylate salts that posses a non-acicular morphology and have improved properties, such as stability and solubility.

SUMMARY

The present invention relates to flupirtin carboxylate acid addition salts having the following formula (2), (2)

wherein R represents hydrogen or a $C_1$-$C_6$ alkyl group, excluding $C_1$-$C_6$ alkyl group that are of maleate and gluconate flupirtine salts.

In another embodiment, the acid addition salts having the formula (2) may be prepared by a process comprising reacting flupirtine base (2-amino-3-carbethoxyamino-6-p-fluorobenzylamino-pyridine) and a carboxylic acid having the following formula

HOOC—R providing a reaction mixture from which the said acid addition salt precipitates, wherein R represents a hydrogen or a $C_1$-$C_6$ alkyl group excluding $C_1$-$C_6$ alkyl group that are of maletae and gluconate flupirtine salts.

In one embodiment, the present invention provides pharmaceutical compositions comprising at least one of the above flupirtine acid addition salts and at least one pharmaceutically acceptable excipient.

In another embodiment, the present invention also encompasses a pharmaceutical composition comprising at least one of the above described flupirtine acid addition salts prepared according to the processes of the present invention, and at least one pharmaceutically acceptable excipient.

In another embodiment, the invention encompasses a process for preparing a pharmaceutical composition comprising at least one of the above-described acid addition salts, and at least one pharmaceutically acceptable excipient.

In another embodiment, the invention encompasses the use of at least one of the above described flupirtine acid addition salts for the manufacture of a medicament for treatment and prevention of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis.

In another embodiment, the invention encompasses the use of at least one of the above described flupirtine acid addition salts for the manufacture of a pharmaceutical composition.

In yet another embodiment, the invention encompasses a method of treating and preventing of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis, comprising administering a pharmaceutical composition comprising at least one of the above described flupirtine acid addition salts to a patient in need thereof.

DETAILED DESCRIPTION

As referred to herein, the "aspect ratio" denotes the ratio of the second largest dimension of a crystal particle (i.e. its width) to the largest dimension of the crystal particle (i.e. its length). The aspect ratio may be determined from a representative number of crystals by visual observation under a light microscope.

As referred to herein, the term "non-acicular crystals" denotes crystalline particles having an aspect ratio of 0.2 or greater. Preferably, the aspect ratio is between 0.2 and 1.0, preferably between 0.3 and 0.9, more preferably between 0.4 and 0.8, and most preferably between 0.6 and 0.7.

As referred to herein, the term "crystalline particles" preferably denotes crystalline flupirtine acid addition salts characterized as having a mean particle size of greater than 30 μm. Preferably, the mean particle size is greater than 50 μm, more preferably greater than 100 μm, even more preferably greater than 150 μm, and most preferably greater than 200 μm. Furthermore, for reasons of formulation efficiency, it is preferred that the mean particle size is less than 1000 μm, preferably less than 500 μm, even more preferably less than 300 μm, and most preferably less than 250 μm.

As defined herein, the term "particle size" refers to the size of the largest dimension of a crystal particle, and the mean particle size is determined from a representative number of crystals. The particle size may be determined by visual observation under a light microscope.

As referred to herein, the term "storage form" denotes a flupirtine salt to which the free flupirtine base is converted by acidification for the purpose of later conversion of said salt to another flupirtine salt. For example, according to the above definition, flupirtine acetate would be a storage form of flupirtine base if flupirtine acetate is produced and subsequently converted, via the base, to e.g. flupirtine gluconate.

The present invention relates to carboxylate acid addition salts of flupirtine that posses a non-acicular morphology in contrast to the previously known salts of flupirtine, i.e., these salts of the present invention crystallise as polygons, platelets, cubes or short columns. This is surprising since, as described in Chemiker Zeitung 105: 217-219, 1981, the linear structure of flupirtine free base and of flupirtine hydrochloride is thought to induce the formation of needle-like crystals.

The present invention relates to flupirtine carboxylate acid addition salts having the following formula (2), (2)

wherein R represents hydrogen or a $C_1$-$C_6$ alkyl group excluding $C_1$-$C_6$ alkyl group that are of maletae and gluconate flupirtine salts.

Preferably, the salts of formula (2) have a non-acicular morphology.

Preferably, the $C_1$-$C_6$ alkyl group is a saturated $C_1$-$C_6$ alkyl group excluding $C_1$-$C_6$ alkyl group of gluconate flupirtine salt.

Suitable saturated $C_1$-$C_6$ alkyl group comprise methyl, ethyl, n-propyl, iso-propyl, n-butyl, sec-butyl, tert-butyl, pentyl and hexyl.

Preferably, the acid is formic, acetic or propionic acid, more preferably, acetic or propionic acid.

In the above acid addition salt of formula (2), the mole ratio of the acid component to the flupirtine base component is 1:1 to 1:1.3, preferably 1:1.2, more preferably 1:1 to 1:1.1, and most preferably 1:1, respectively.

The present invention also relates to a population of the above flupirtine carboxylate acid addition salts characterized in that at least 50 mol-%, preferably at least 60 mol-%, more preferably at least 70 mol-%, even more preferably at least 80 mol-% and most preferably at least 90 mol-% of the crystalline particles have crystallized in the form of non-acicular crystals as defined above.

Figure 1:
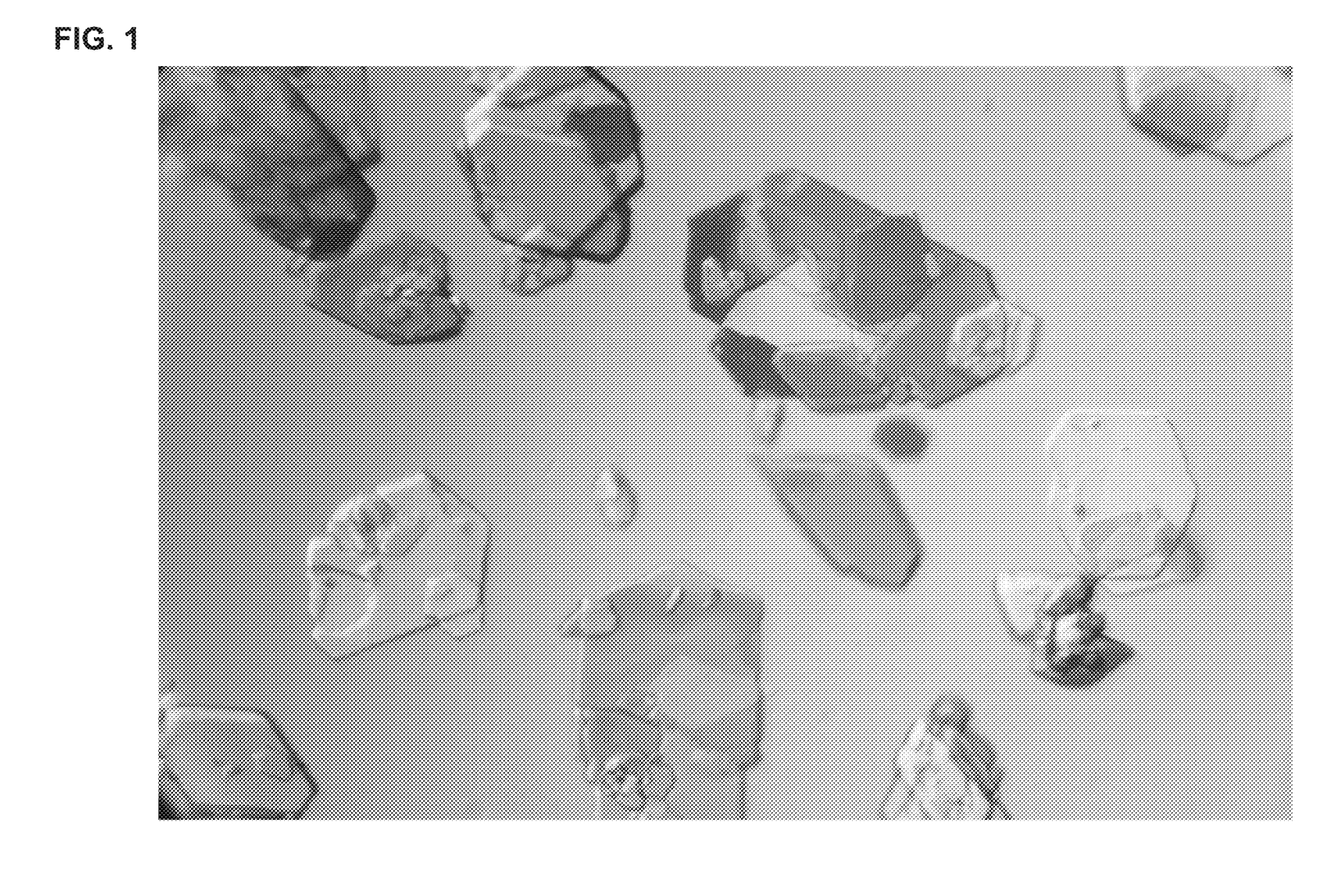
FIG. 1 depicts a photomicrograph of flupirtine acetate.
Figure 2:
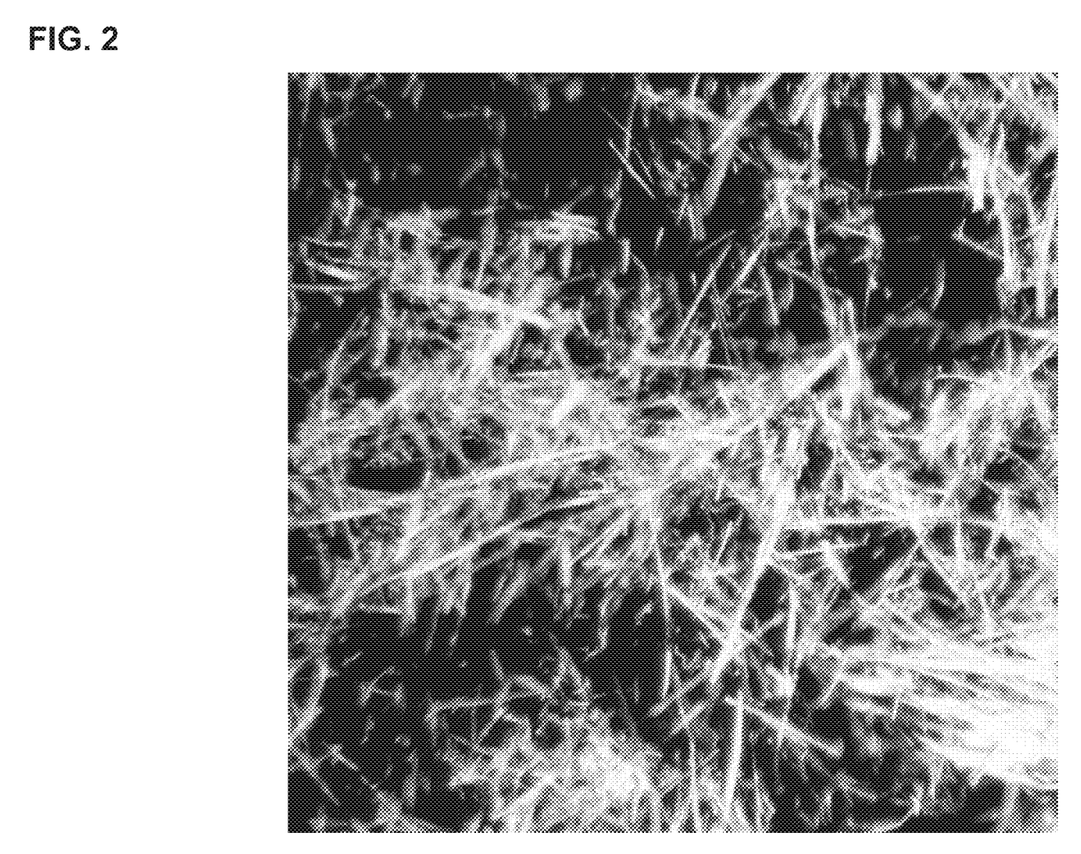
FIG. 2 depicts a photomicrograph of flupirtine maleate.

The non-acicular morphology of the salts of the invention can be exemplified by comparison of flupirtine acetate to flupirtine maleate as depicted in FIGS. 1 and 2, respectively (and see example 3).

The non-acicular morphology of the above flupirtine salts also results in a much higher bulk density as is also evident from the table in example 5. This is advantageous for packing and for controlled release formulations, since polygons and hexagons are more easily coated than acicular crystals and, thus, the formulation difficulties inherent to prior used acicular flupirtine salts are also overcome.

Furthermore, the markedly less acicular morphology of the crystals allows better flowability and dosing. Thus, the hexagonal or polygonal crystal shape of these flupirtine salts overcomes the processing difficulties inherent to acicular flupirtine salts such as flupirtine maleate.

In contrast to other acid addition salts, for example, maleate and gluconate, the carboxylic acid addition salts of flupirtine of the present invention, especially acetate and the propionate, show substantially improved stability towards oxidation (see example 6) and towards discoloration, when exposed to air for a storage period of 30 days at room temperature. Discoloration can take takes place after prolonged storage or when exposed to air. Discoloration is regarded as leading to an active pharmaceutical ingredient (API) of low pharmaceutical quality and can be avoided by using a protective atmosphere in the production process and using expensive packaging materials for the finished drug forms. The discoloration effect is known for flupirtine hydrochloride, flupiritine gluconate and both polymorphs of flupirtine maleate.

These properties make the oxidation stable flupirtine salts of formula (2) ideally suited as storage form.

Further, the above salts are exceptionally more soluble in ethanol and other alcohols than the prior known flupirtine acid addition salts (see example 7).

Accordingly, the alcohol component comprises at least 10 wt-%, preferably at least 20 wt-%, even more preferably at least 30 wt-%, and most preferably at least 40 wt-%, of the total weight of the solvents.

Preferred alcohols are pharmaceutically acceptable alcohols as are known in the art. Preferred examples include propylene glycol, ethanol, 2-(2-ethoxyethoxy)ethanol, benzyl alcohol, glycerol, glycofurol, polyethylene glycol 200, and the like. More preferred is ethanol.

The acid addition salts having the following formula (2) may be prepared by a process comprising reacting free flupirtine base (2-amino-3-carbethoxyamino-6-(4-fluorobenzylamino-pyridine) and a carboxylic acid providing a reaction mixture from which the said acid addition salt precipitates.

The free flupirtine base can be prepared by known processes as are described, for example, in European patent no. EP 0 977 736, example 2.

In some embodiments, a solution comprising flupirtine base and a solvent is reacted with the acid thus providing the said reaction mixture, in others, flupirtine base, the acid and the solvent are combined providing the said reaction mixture.

In some preferred embodiments, the acid is dissolved in a solvent prior to the reaction with flupirtine base; in others the acid is reacted neat, i.e., without a solvent.

The solution can be prepared by combining flupirtine base and the solvent. Preferably, this combination is heated to aid in dissolution, if required. Preferably, heating is to a temperature of about 30° C. to about 80° C., more preferably, to about 60° C. Preferably, to avoid oxidation, a protective atmosphere like nitrogen or argon may be used in this reaction.

Examples for suitable solvents include but not limited to ethers, alcohols, ketones, esters, halogenated solvents, nitriles, water or mixtures thereof.

Preferably, the ethers are $C_3$-$C_7$ ethers, the alcohols are $C_1$-$C_5$ alcohols, the ketones are $C_3$-$C_5$ ketones, the esters are $C_2$-$C_6$ esters, the halogenated solvents are $C_1$-$C_6$ halogenated solvents, the nitriles are $C_2$-$C_3$ nitriles. More preferably, the $C_1$-$C_6$ halogenated solvents are $C_1$-$C_3$ chlorinated solvents and the $C_2$-$C_6$ esters are $C_2$-$C_6$ acetates.

Preferably, the $C_3$-$C_7$ ethers are diethyl ether, diisopropyl ether, t-butyl methyl ether, or mixtures thereof. Preferably, the $C_1$-$C_5$ alcohols are methanol, ethanol, isopropanol, n-propanol, n-, iso-, or tert-butanol, or mixtures thereof. Preferably, the $C_3$-$C_5$ ketones are acetone, methyl ethyl ketone, diethyl ketone, or mixtures thereof. Preferably, the $C_1$-$C_6$ halogenated solvents are dichloromethane, chloroform or chlorobenzene, or mixtures thereof, the $C_2$-$C_3$ nitriles are acetonitrile, propionitrile, or mixtures thereof; the $C_2$-$C_6$ acetates are methyl-, ethyl-, n-propyl-, i-propyl-, butyl-acetate or mixtures thereof. Most preferably, the $C_1$-$C_5$ alcohols are methanol, ethanol or iso-propanol or mixtures thereof. Most preferably, the solvent is a $C_1$-$C_5$ alcohol, more preferably ethanol or iso-propanol.

It is further preferred that the flupirtine base is reacted with about 1 to about 1.3 mole equivalents, preferably about 1 to about 1.2 mole equivalents, and most preferably about 1 to about 1.1 mole equivalents, of the corresponding carboxylic acid per mole equivalent of flupirtine base. Preferably, the carboxylic acid is acetic acid or propionic acid.

Preferably, the said reaction mixture is preferably a solution from which the acid addition salt precipitates.

Precipitation occurs either on its own motion or is induced by reducing the solvent volume and/or the temperature and/or by adding an anti solvent and/or by adding seeding crystals.

Typically, the anti-solvent is such that is less polar than the reaction solvent and thus when added leads to the formation of a precipitate of the said salt. Examples for such solvent can be anyone of the above and also toluene, benzene, hexane, cyclohexane and pentane.

Preferably, the temperature is reduced to about 0° C. to about −15° C.

The precipitated salt is collected by filtration and drying, optionally followed by further purification steps. Preferably, drying is performed under reduced pressure for about 12 hours.

According to this procedure flupirtine salts of high purity are obtained. Preferably the purity is of more than about 95 area percent as measured by HPLC. Thus, these salts are especially suitable for the purification of flupirtine base since they crystallize in polygonal dense shapes and are less likely to contain enclosures of solvents and/or impurities.

The structure and composition of the obtained salts prepared can be confirmed by analytical methods such as NMR spectrometry, IR spectrometry, elemental analysis, DSC analysis, and the determination of the melting point (see examples 1 and 2 and FIGS. 3-8).

The salts prepared by the method described above can be further purified by recrystallization from appropriate solvents, if necessary. Examples for such solvents include isopropanol, acetone, methylene chloride and chloroform.

Furthermore, the salts of the invention can further be purified by conversion to the flupirtine free base, followed by extraction or crystallization and renewed acidification.

In the above process, when the acid is acetic acid and the solvent is at least one of ethers, alcohols, ketones, esters, halogenated solvents, nitriles, water or mixtures thereof, a crystalline form of flupirtine acetate is obtained. The preferred list of solvents is mentioned before.

Figure 3:
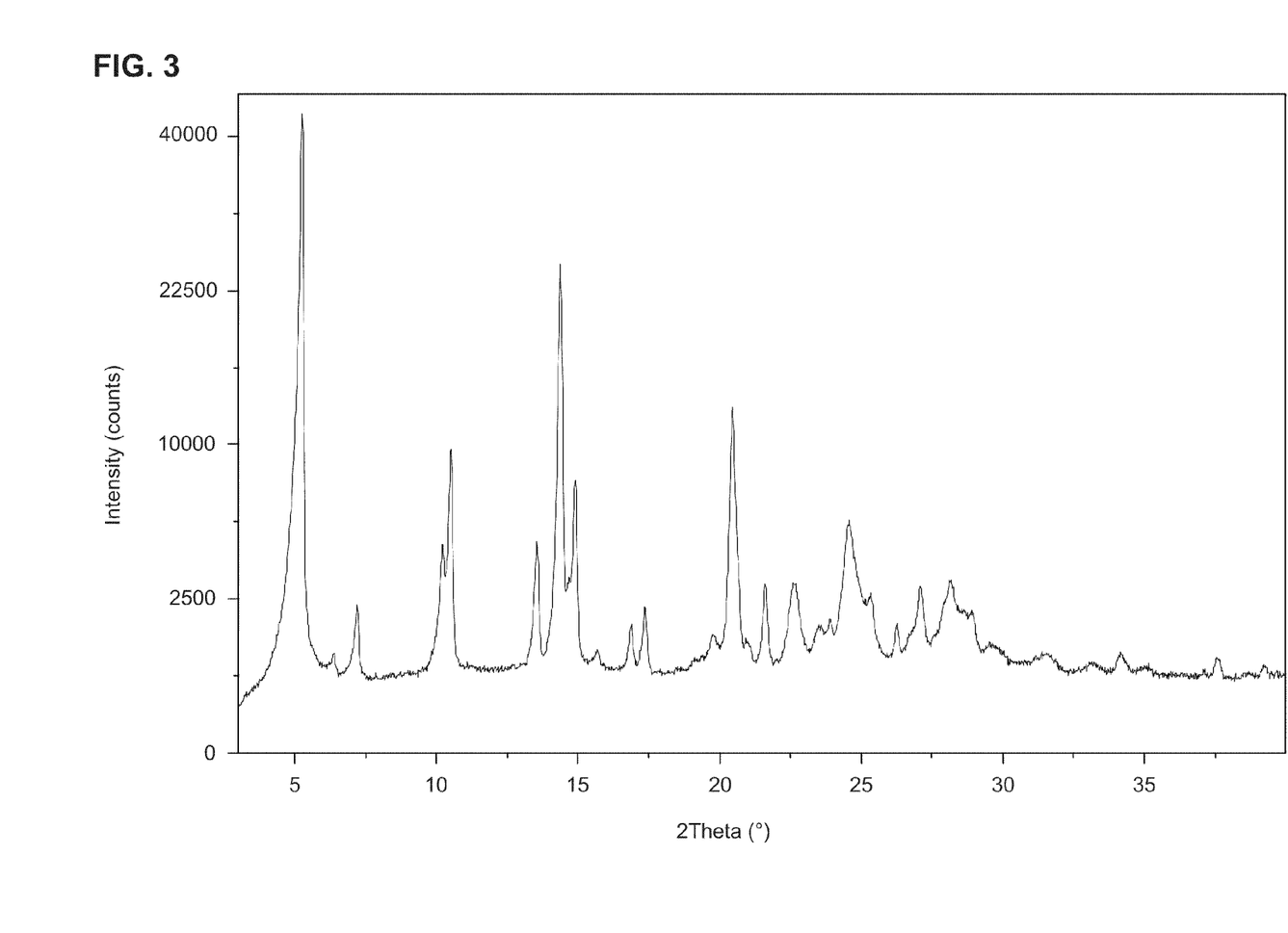
FIG. 3 depicts an X-ray powder diffraction pattern of flupiritine acetate.

In one embodiment, the present invention provides a crystalline form of flupirtine acetate characterized by data selected from the group consisting of: FIG. 1, a powder XRD pattern with peaks at about 5.3, 10.5, 14.4, 20.4 and 24.5±0.2 degrees two theta, a powder XRD pattern as depicted in FIG. 3; and a combination thereof.

Figure 4:
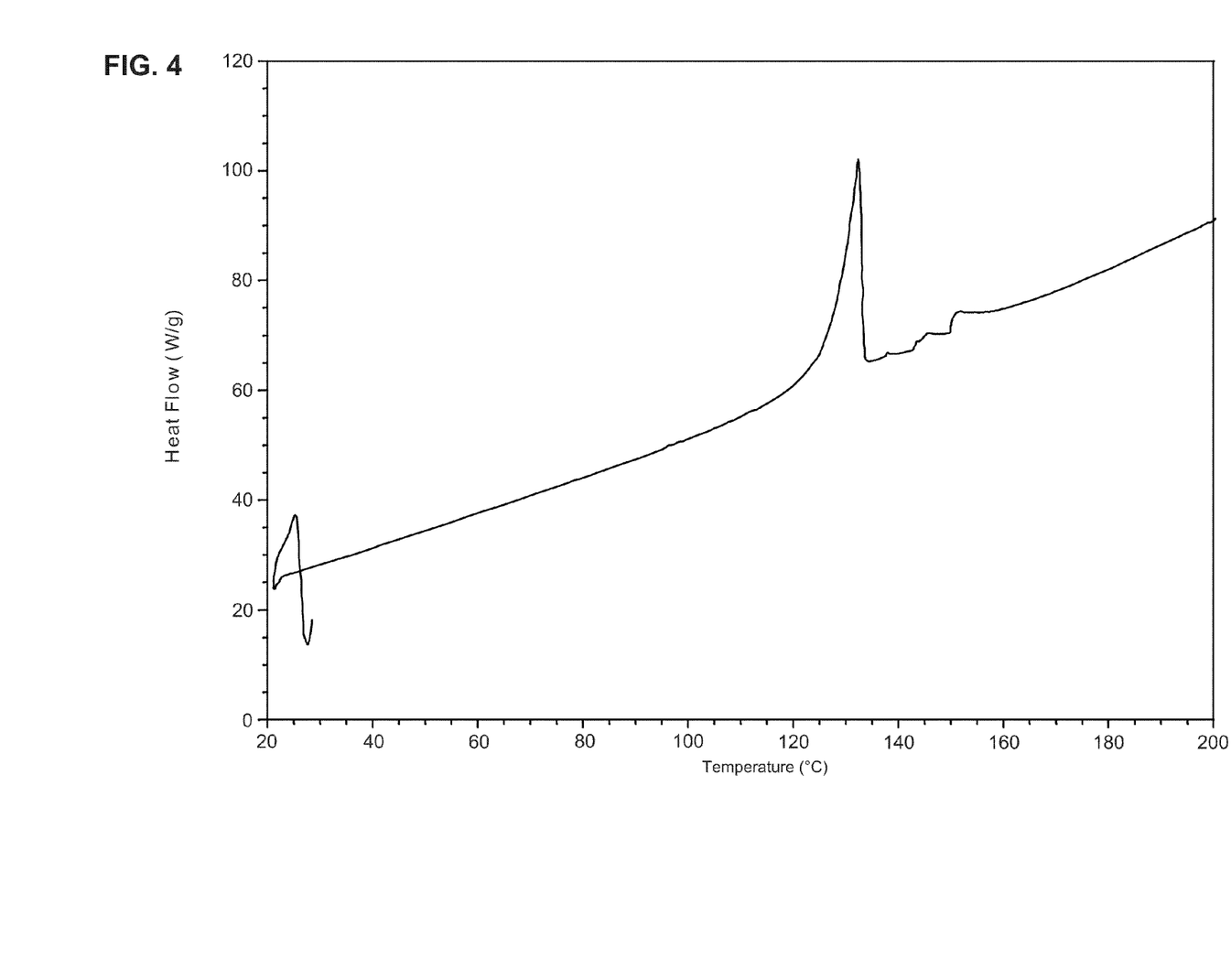
FIG. 4 depicts a DSC thermogram of flupirtine acetate.
Figure 5:
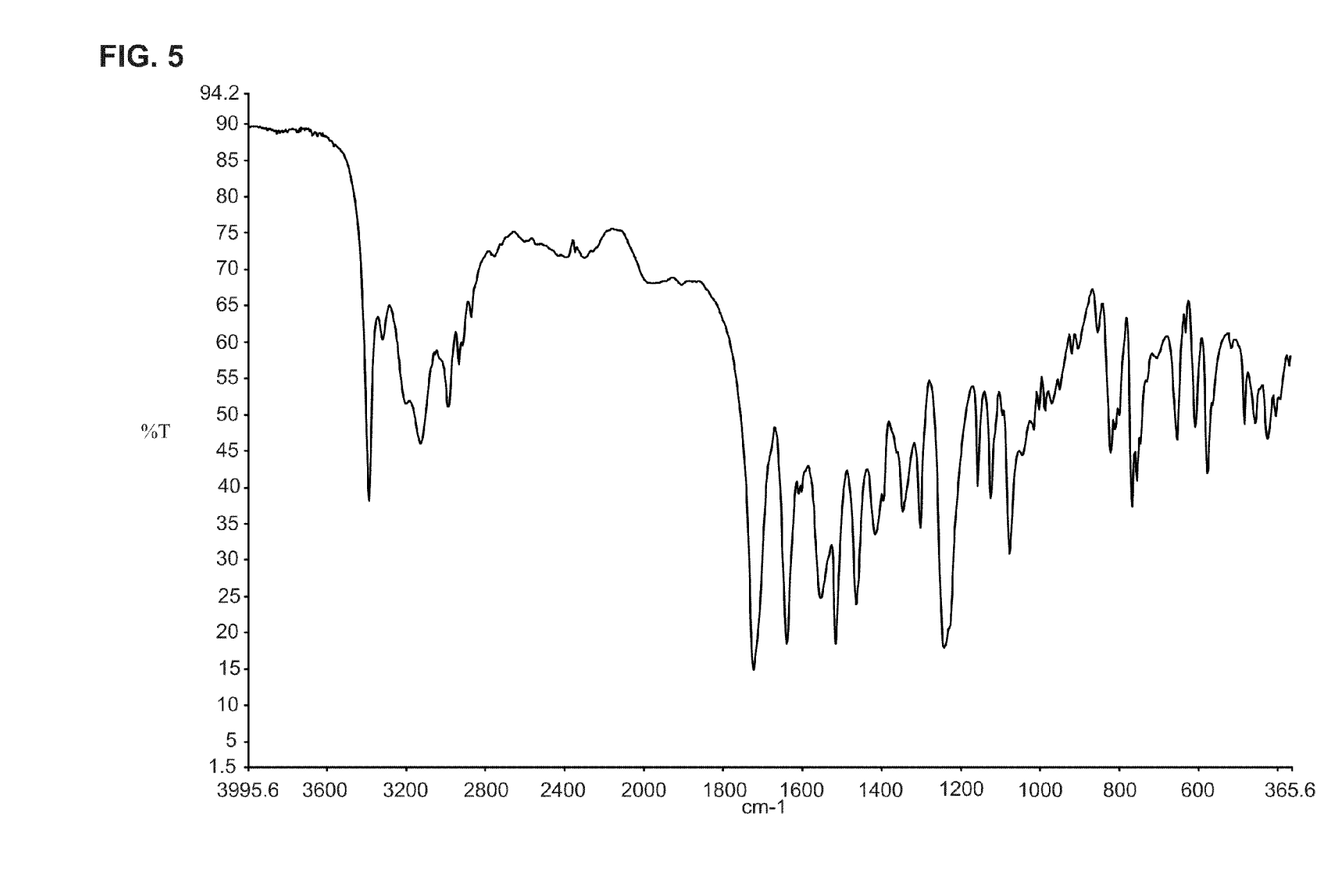
FIG. 5 depicts an IR spectrum of flupiritine acetate.

The above crystalline form of flupirtine acetate can be further characterized by data selected from the group consisting of: a powder XRD pattern with peaks at about 7.2, 13.5, 14.9, 17.4, 21.6 and 27.1±0.2 degrees 2-theta, a DSC peak at about 132±2° C., a DSC pattern as depicted in FIG. 4, a FT-IR spectrum with peaks at about 3389, 3129, 2986, 1725, 1641, 1555 and 1518 cm$^{-1}$±2 cm$^{-1}$, and an IR pattern as depicted in FIG. 5; and a combination thereof.

In the above process, when the acid is propionic acid and the solvent is at least one of ethers, alcohols, ketones, esters, halogenated solvents, nitriles, water or mixtures thereof. a crystalline form of flupirtine propionate is obtained. The preferred list of solvents is mentioned before.

Figure 6:
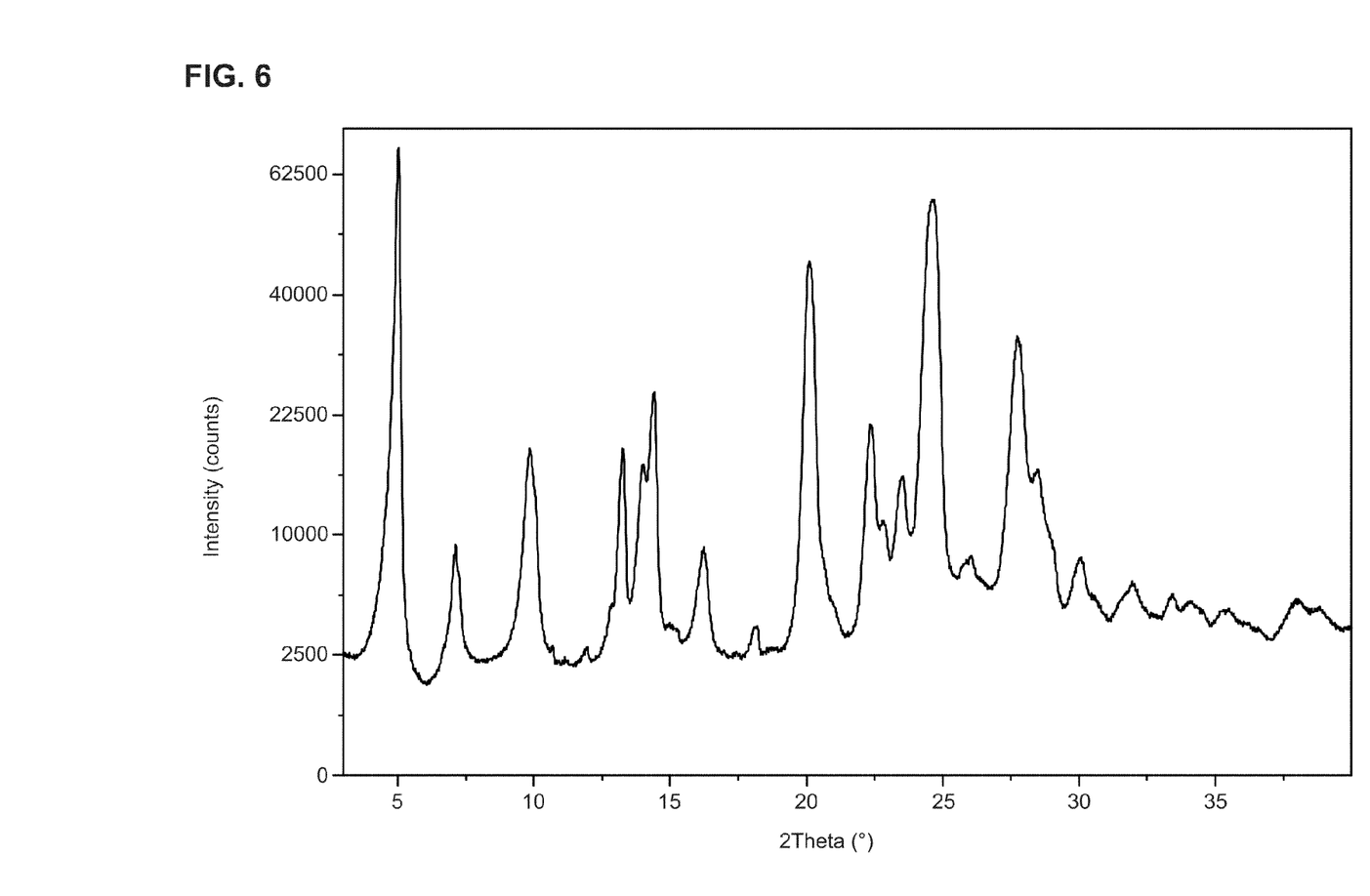
FIG. 6 depicts a X-ray powder diffraction pattern of flupiritine propionate.

In one embodiment, the present invention provides a crystalline form of flupirtine propionate is characterized by data selected from the group consisting of: a powder XRD pattern with peaks at about 5.1, 13.3, 14.4, 24.4 and 27.7±0.2 degrees two theta, a powder XRD pattern as depicted in FIG. 6; and a combination thereof.

Figure 7:
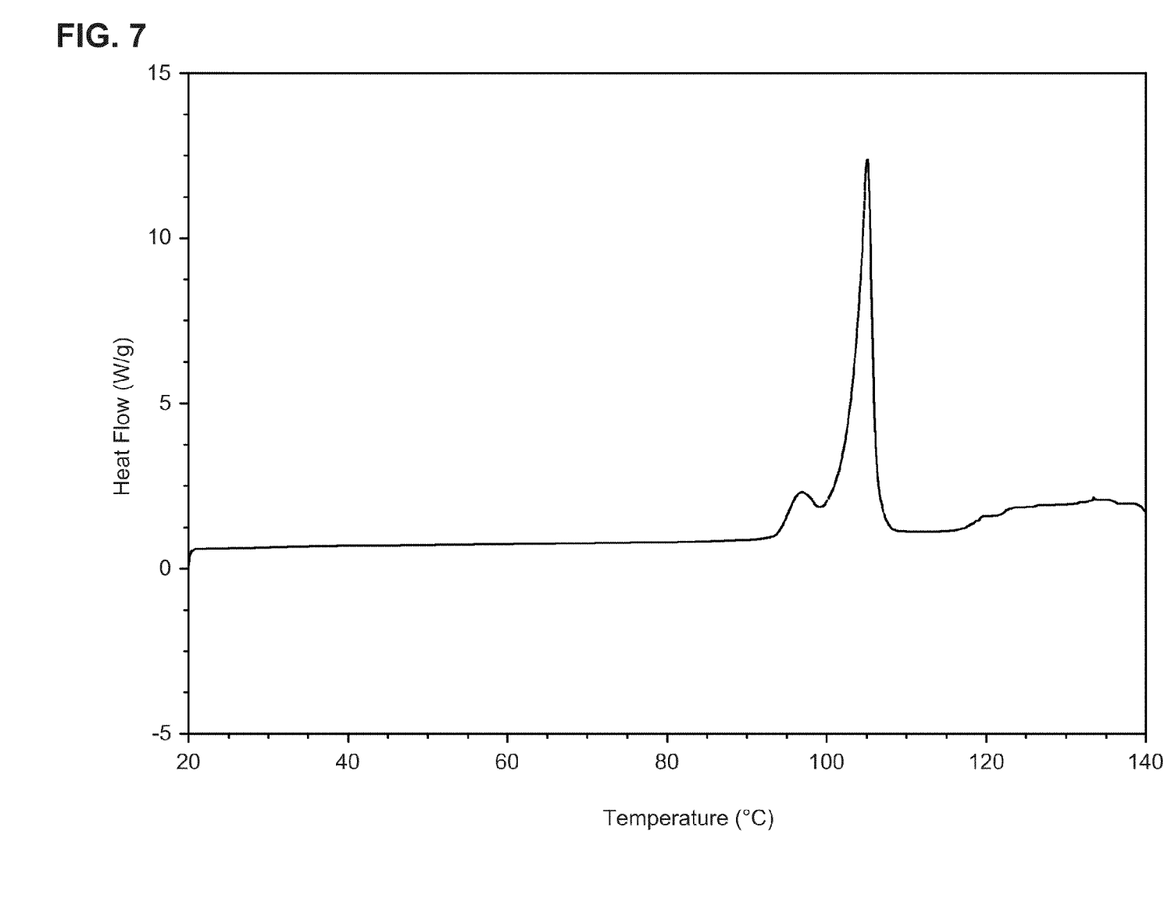
FIG. 7 depicts a DSC thermogram of flupirtine propionate.

The above crystalline form of flupirtine propionate can be further characterized by data selected from the group consisting of: a powder XRD pattern with peaks at about 7.1, 9.8, 16.2 and 22.4±0.2 degrees two-theta, a FT-IR spectrum with peaks at about 3394, 2991, 1721, 1643, 1464 and 1245±2 cm$^{-1}$, and an IR pattern as depicted in FIG. 7; and a combination thereof.

Also, the salts of the invention and also their crystalline forms are particularly well suited for pharmaceutical formulations, i.e., solid or liquid pharmaceutical formulations. The crystals of the salts of the present invention are more easily coated and, thus, the formulation difficulties inherent to prior compositions utilizing acicular flupirtine salts are overcome.

In one embodiment, the present invention provides pharmaceutical compositions comprising at least one of the above flupirtine acid addition salts and at least one pharmaceutically acceptable excipient. Optionally, prior known flupirtine salts such as flupirtine maleate and gluconate can also be used in addition to the compounds of the invention.

The pharmaceutical composition of the invention may also comprise one or more auxiliary excipients such as for example carriers, diluents, binders, lubricants, surfactants, disintegrants, plasticizers, anti-tack agents, opacifying agents, pigments, anti-oxidants and the like. As will be appreciated by those skilled in the art, the exact choice of excipient and relative amount will depend on the type of pharmaceutical composition, the API, dosage and other factors.

In another embodiment, the present invention also encompasses a pharmaceutical composition comprising at least one of the above described flupirtine acid addition salts prepared according to the processes of the present invention, and at least one pharmaceutically acceptable excipient.

In another embodiment, the invention encompasses a process for preparing a pharmaceutical composition comprising at least one of the above-described acid addition salts, and at least one pharmaceutically acceptable excipient.

In another embodiment, the invention encompasses the use of at least one of the above described flupirtine acid addition salts for the manufacture of a medicament for the treatment and prevention of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis.

In another embodiment, the invention encompasses the use of at least one of the above described flupirtine acid addition salts for the manufacture of a pharmaceutical composition.

In yet another embodiment, the invention encompasses a method of treating and preventing of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis, comprising administering a pharmaceutical composition comprising at least one of the above described flupirtine acid addition salts to a patient in need thereof.

The present invention can be further illustrated by the following Figures and non-limiting Examples.

EXAMPLES

HPLC Method

| Column | Reversed phase silica gel column | |
|---|---|---|
| Mobile Phase A | MeCN-10%/0.02M NH4H2PO4 aq | |
| Mobile Phase B | MeCN-80%/0.02M NH4H2PO4 aq | |
| Gradient | Time (min) | Mobile Phase A (% vol/vol) | Mobile Phase B (% vol/vol) |
| | 0 | | 0 |
| | 2 | | 0 |
| | 10 | | 15 |
| | 50 | | 100 |
| | 55 | | 100 |
| | 56 | | 0 |
| | 61 | | 0 |
| Flow Rate | 1.0 ml/min | |
| Detector | λ = 248 nm; | |
| Column Temperature | Room temperature (25° C.) | |
| Injection Volume | 20 μl | |

Melting Point

Melting point was measured with the Mettler-Toledo FP apparatus.

X-Ray Powder Diffraction Analysis (XRPD)

XPRD was measured with a Philips X'Pert PRO powder diffractometer with the following parameters.

| Sample holder preparation | Samples after being powdered in a mortar and pestle are applied directly on silicon PW1817/32 "zero background" holder |
|---|---|
| Instrument | Philips X'Pert PRO |
| Goniometer | PW3050/60 |
| Generator | PW3040; 45 kV, 40 mA |
| X-Ray tube | PW3373/00; Cu anode LFF |
| X-ray radiation | λ(CuKα$_1$) = 1.540598 Å |
| Temperature | 295 ± 5° K |

Differential Scanning Calorimetry (DSC) Analysis

DSC was measured using a TA Instrument, scanning from 20° C. to 100° C. at a scan rate of 10° C./minute. A sample was placed in a closed aluminum pan and the reference pan was prepared the same.

Example 1

Preparation of 2-amino-3-carbethoxyamino-6-(4-fluoro-benzylamino)-pyridine acetate Under nitrogen atmosphere 40 g of 2-amino-3-carbethoxyamino-6-(4-fluoro-benzylamino)-pyridine were dissolved in 1100 ml of Ethanol (90%) at 60° C. 8 g of acetic acid were dissolved in 200 ml of ethanol at 20° C. The mixture was cooled down to 40° C. While stirring the solution of acetic acid was added. The solution was filtered at 20° C. and crystallisation occurred while cooling the solution down to −15° C. for 24 h. The product was collected by filtration and dried at reduced pressure at room temperature for 12 h. As a result of drying 38.0 g white crystals of the product were obtained.

$^1$H-NMR (DMSO-d6, 400 Mhz): 1.19 (3H, s, 21-CH$_3$), 1.90 (3H, s, 26-CH$_3$), 4.01-4.03 (2H, m, 20-CH$_2$), 4.33-4.35 (2H, d, J=8 Hz, 12-CH$_2$), 5.20 (2H, s, 7-NH$_2$), 5.65-5.67 (1H, d, 5-CH), 6.53 (1H, s, br, 11-NH), 6.99-7.01 (1H, m, 4-CH), 7.07-7.11 (2H, t, J=8 Hz, 15/17-CH), 7.32-7.35 (2H, m, 14/18-CH), 8.18 (1H, s, 8-NH).

m.p. 131-132° C.

Example 2

Preparation of 2-amino-3-carbethoxyamino-6-(4-fluoro-benzylamino)-pyridine propionate Under nitrogen atmosphere 30 g of 2-amino-3-carbethoxyamino-6-(4-fluoro-benzylamino)-pyridine and 7.5 g of propionic acid were added to 500 ml of isopropanol. The mixture was heated to 60° C. A transparent solution of flupirtine propionate was formed and was kept for 30 min at 50° C. The solution was filtered at 20° C. and crystallisation occurred while cooling the solution down to −5° C. for 12 h. The product was collected by filtration and dried at reduced pressure at room temperature for 12 h. As a result of drying 25 g white crystals of the product were obtained.

$^1$H-NMR (DMSO-d6, 400 Mhz): 0.97 (3H, t, J=8 Hz, 22-CH$_3$), 1.17-1.20 (3H, m, 21-CH$_3$), 2.17-2.21 (2H, m, 23-CH$_2$), 3.99-4.02 (2H, m, 20-CH$_2$), 4.34 (2H, d, J=8 Hz, 12-CH$_2$), 5.21 (2H, s, 7-NH$_2$), 5.66 (1H, d, J=8 Hz, 5-CH), 6.55-6.56 (1H, m, 11-NH), 7.00 (1H, d, br, J=8 Hz, 4-CH$_2$), 7.09 (2H, t, J=8 Hz, 15/17-CH), 7.31-7.35 (2H, m, 14/18-CH), 8.19 (1H, s, 8-NH).

m.p. 102.0° C.

Example 3

Preparation of FIGS. 1 and 2

The photomicrographs were obtained by gently exerting pressure on the sample material with a mortar and pistil, transferring the sample material to a microscope slide and covering it with immersion oil, followed by observation and image recording on an Optech Biostar microscope equipped with a polarisation filter. The magnification was 200, i.e. at a width of the photomicrograph of 14 cm, 1 cm of said photograph corresponds to about 0.06 mm.

Example 4

Preparation of Flupirtine Maleate Form A According to U.S. Pat. No. 5,959,115, Example 3

Figure 8:
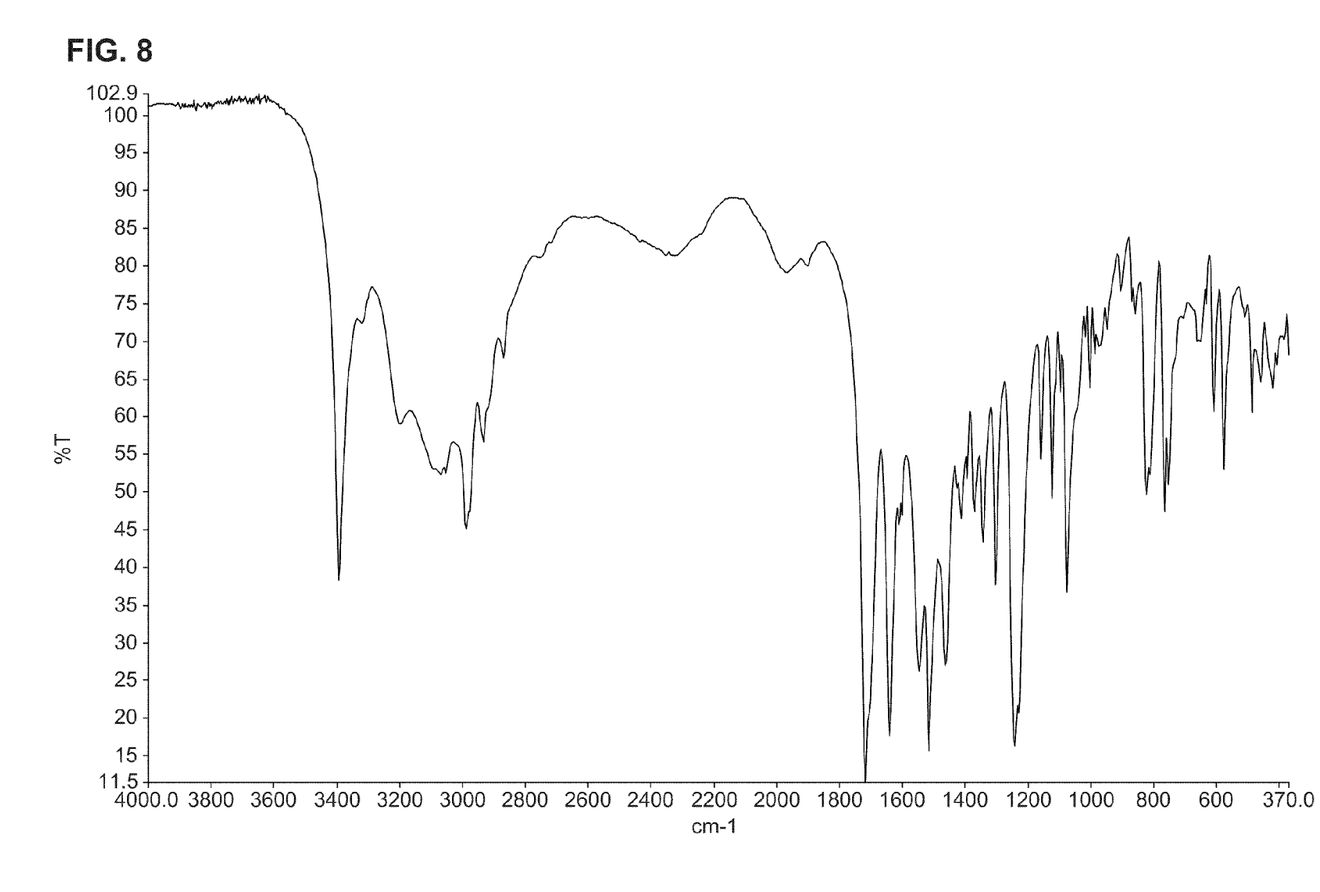
FIG. 8 depicts an IR spectrum of flupirtine propionate.

Preparation of the Pure A Modification of Flupirtine Maleate Dried flupirtine maleate which was crystallized from isopropanol and contained 10% of the A modification in addition to 90% of the B modification (FIG. 8, bottom curve) was dispersed in isopropanol in a ratio of 1:0.8. After stirring had been carried out for 200 minutes at 20° C., the characteristic strong B reflection at 5.5°2 I had disappeared and only the characteristic reflections of the A modification at 6.9 and 9.2°2 I were observed (FIG. 8, middle curve).

Example 5

Preparation of Flupirtine Maleate Form B 30 g of Flupirtine base were dissolved in 1080 ml of Isopropanol at 60° C. 12.8 g of Maleic acid was dissolved in 96 ml of Isopropanol. 0.2 g of flupirtine maleate B crystals made according EP 977 736 patent were added. Flupirtine maleate B was made according EP 977 736 through heating of part of maleat A for 2 h at 150° C. Maleic acid solution was added to Flupirtine solution at 60° C. in the course of stirring. The mixture was stirred for 2 minutes and cooled down to 17° C. The sediment formed was filtered. The color of the sediment was white. 40.9 g of the product was formed.

Example 6

Determining the Bulk Density of Flupirtine Salts

| Salt form | Crystal shape | Bulk density (ml/100 g substance) |
|---|---|---|
| Maleate Form A | Fine needles | 686 |
| Maleate Form B | Very fine needles | 1634 |
| Acetate | Hexagons and polygonal plates | 330 |
| Propionate | Hexagons and polygonal plates | 306 |

The bulk density was determined as follows: Without increasing its density, sample material (about 4 grams) was introduced into a 10 ml measuring cylinder (±0.2 ml). The volume and the exact weight of the introduced sample material were determined. The bulk density was calculated as volume per 100.0 g of sample material.

Example 7

Storage Stability of Flupirtine Salts

HPLC was performed after preparation of the salts and repeated after 14 days of storage at room temperature under normal air containing about 21% oxygen.

| Salt form | Flupirtine signal after 0 days (area under the peak in %) | Flupirtine signal after 14 days (area under the peak in %) |
| --- | --- | --- |
| Flupirtine maleate A | 99.27 | 96.18 |
| Flupirtine maleate B | 99.12 | 95.92 |
| Flupirtine acetate | 99.54 | 98.64 |

As is evident from the table, the area under the peak of the flupirtine signal decreased by 3.11% for flupirtine maleate form A and by 3.22% for flupirtine maleate form B as compared to only 0.9% of flupirtine acetate.

Example 8

Dissolution Profiles of Flupirtine Acid Addition Salts in Ethanol

The dissolution in Ethanol was measured using compacted substance.
Compaction:
100 mg substance was compacted using a hydraulic press. Diameter of cake: 8.9 mm; pressure 20 kp/cm$^2$ for 15 sec.
Liberation parameter:
Basket, 50 UpM, 1000 ml medium 37° C. Apparatus: DT6R Dissolution Tester (ERWEKA).
At given time points 5.0 ml solution were taken and measured vs. reference at 244 nm at a spectral photometer. The solution was refilled with 5 ml solvent. The amount of liberated substance at given time points was calculated using a response factor (absorption/mg substance). Measuring error: 10%.

| Sample taken | Amount of substance dissolved (mg) | | | | |
| --- | --- | --- | --- | --- | --- |
| (min) | Acetate | Triflutate | Propionate | Maleate A | Maleate B |
| 0 | | | | | |
| 5 | 50.3 | 98.5 | 110.0 | 2.1 | 4.2 |
| 10 | 108.3 | 115.1 | 109.4 | 4.1 | 6.3 |
| 15 | 103.0 | 108.0 | 110.3 | 6.5 | 12.1 |
| 20 | 95.8 | 107.7 | 107.4 | 9.5 | 16.5 |
| 25 | 96.2 | | 109.6 | 11.7 | 21.3 |
| 30 | 108.3 | | 110.9 | 14.3 | 27.4 |
| 60.25 | 99.7 | | 112.2 | 24.2 | 69.5 |

Similarly to the propionate salt, the triflutate salt of flupirtine, prepared according example 9, was completely dissolved after 10 min stirring in Ethanol.

Example 9

Preparation of Flupirtine Triflutate 12 g of trifluoroacetic acid (TFA) were added to a solution of 30 g of 2-amino-3-carbethoxyamino-6-(4-fluoro-benzylamino)-pyridine in 200 ml of isopropanol at 30° C. The solution was stirred for 30 min. Then it was cooled down to −5° C. and kept for 12 h at this temperature.

The product was collected by filtration and dried at reduced pressure at room temperature for 12 h. As a result of drying 21.0 g white crystals of the product were obtained.

What is claimed is:

1. A crystalline form of flupirtine acetate characterized by data selected from the group consisting of: a powder XRD pattern with peaks at about 5.3, 10.5, 14.4, 20.4 and 24.5±0.2 degrees two theta, a powder XRD pattern as depicted in FIG. 3; and a combination thereof.

2. A crystalline form of flupirtine propionate characterized by data selected from the group consisting of: a powder XRD pattern with peaks at about 5.1, 13.3, 14.4, 24.4 and 27.7±0.2 degrees two theta, a powder XRD pattern as depicted in FIG. 6; and a combination thereof.

3. A pharmaceutical composition comprising a crystalline form of flupirtine acetate according to claim 1, and at least one pharmaceutically acceptable excipient.

4. A pharmaceutical composition comprising a crystalline form of flupirtine propionate according to claim 2, and at least one pharmaceutically acceptable excipient.

5. A method of treating or preventing acute or chronic pain, pain associated with degenerative or inflammatory joint disease, muscular tension, muscle spasm, muscle stiffness, neurodegenerative disorders, back pain, dementia, encephalopathy, diseases of the eye, myocardial ischemia or infarction, cerebral ischemia or infarction, shock, tinnitus or hepatitis, comprising administering a pharmaceutical composition according to claim 3 or claim 4, to a patient in need thereof.

* * * * *